(12) United States Patent
Kirihata et al.

(10) Patent No.: US 8,907,128 B2
(45) Date of Patent: Dec. 9, 2014

(54) BORON COMPOUND WITH AMINO ACID SKELETON CONTAINING CYCLO RING-TYPE RING

(75) Inventors: Mitsunori Kirihata, Osaka (JP); Yoshihide Hattori, Osaka (JP); Kohki Uehara, Osaka (JP); Hiroshi Takenaka, Osaka (JP)

(73) Assignee: Stella Pharma Corporation, Osaka (JP)

( * ) Notice: Subject to any disclaimer, the term of this patent is extended or adjusted under 35 U.S.C. 154(b) by 159 days.

(21) Appl. No.: 13/813,697

(22) PCT Filed: Aug. 2, 2011

(86) PCT No.: PCT/JP2011/067681
§ 371 (c)(1),
(2), (4) Date: May 7, 2013

(87) PCT Pub. No.: WO2012/018015
PCT Pub. Date: Feb. 9, 2012

(65) Prior Publication Data
US 2013/0225861 A1 Aug. 29, 2013

(30) Foreign Application Priority Data
Aug. 3, 2010 (JP) ................. 2010-174537

(51) Int. Cl.
*C07C 5/05* (2006.01)
*C07C 5/02* (2006.01)
*C07F 5/05* (2006.01)
*C07F 5/02* (2006.01)

(52) U.S. Cl.
CPC . *C07F 5/05* (2013.01); *C07F 5/027* (2013.01); *C07F 5/02* (2013.01)
USPC .......................................... 562/507

(58) Field of Classification Search
CPC ............... C07F 5/05; C07F 5/027; C07F 5/02
USPC .......................................... 562/507
See application file for complete search history.

(56) References Cited

U.S. PATENT DOCUMENTS

| 6,037,490 | A  | 3/2000 | Kabalka et al. |
| 8,431,738 | B2 | 4/2013 | Kirihata et al. |
| 2011/0124914 | A1 | 5/2011 | Kirihata et al. |
| 2011/0184175 | A1 | 7/2011 | Kirihata et al. |

FOREIGN PATENT DOCUMENTS

| WO | WO-98/09973 A1 | 3/1998 |
| WO | 2010/010913 A1 | 1/2010 |
| WO | WO-2010/010912 A1 | 1/2010 |

OTHER PUBLICATIONS

International Search Report issued Aug. 30, 2011 during prosecution of International Application No. PCT/JP2011/067681.
Tjarks, Werner; "The Use of Boron Clusters in the Rational Design of Boronated Nucleosides of Neutron Capture Therapy of Cancer"; Journal of Organometallic Chemistry, 2000, vols. 614-615, pp. 37-47.
Imamura, Ken-Ichiro, et al; "Synthesis and in Vitro Evaluation of 5-closo- and 5-nido-Orthocarboranyluridines as Boron Carriers"; Bull. Chem. Soc. Jpn., 1997, vol. 70, No. 12, pp. 3103-3110.
Al-Madhoun, Ashraf S., et al; "Synthesis of a Small Library of 3-(Carboranylalkyl)thymidines and Their Biological Evaluation as Substrates for Human Thymidine Kinases 1 and 2"; J. Med. Chem, 2002, No. 45, pp. 4018-4028.
Compostella, F., et al; "Synthesis of Glycosyl Carboranes with Different Linkers Between the Sugar and the Boron Cage Moieties"; Research and Development in Neutron Capture Therapy, 2002, pp. 81-84.
Kahl, Stephen B., et al; "Synthesis and Properties of Tetrakis-Carborane-Carboxylate Esters of 2,4-BIS-(a,β-Dihydroxyethyl) Deuteroporphyrin IX"; Progress in Neutron Capture Therapy for Cancer, 1992, pp. 223-226.
Cai, Jianping, et al; "Boron-Containing Polyamines as DNA Targeting Agents for Neutron Capture Therapy of Brain Tumors: Synthesis and Biological Evaluation"; J. Med. Chem., 1997, vol. 40, pp. 3887-3896.
Lim, Hong-Gyu, et al; "0-Carboranyl Derivatives of 1,3,5-Triazines"; Research and Development in Neutron Capture Therapy, 2002, pp. 37-42.
Wyzlic, Iwona, et al; "A General, Convenient Way to Carbonate-Containing Amino Acids for Boron Neutron Capture Therapy"; Tetrahedron Letters, 1992, vol. 33, No. 49, pp. 7489-7490.

*Primary Examiner* — Yevengeny Valenrod
(74) *Attorney, Agent, or Firm* — Fulbright & Jaworski LLP

(57) ABSTRACT

The purpose of the present invention is to provide a novel boron-containing compound utilizable in BNCT and so on and a process for preparing same. According to the process, a boron compounds having an amino acid skeleton containing cyclo-type rings or a pharmaceutically acceptable salt thereof is prepared, said boron compound being represented by general formula (I) [wherein l is an integer of 1 to 6; m is 0, 1, or 2; and n is 0, 1 or 2].

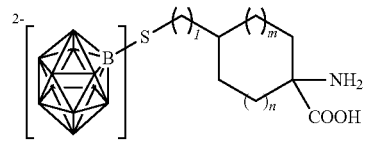

10 Claims, 2 Drawing Sheets

BORON COMPOUND WITH AMINO ACID SKELETON CONTAINING CYCLO RING-TYPE RING

This application is a US §371 application national phase filing of PCT/JP2011/067681, filed Aug. 2, 2011, which claims priority to JP Application No. 2010-174537, filed Aug. 3, 2010, both of which applications are incorporated by reference herein in their entirety.

TECHNICAL FIELD

The present invention relates to a boron compound having an amino acid skeleton containing a cyclo-type ring and a method for producing same. There are various applications for boron compounds with amino acid skeletons containing cyclo-type rings in accordance with the present invention. For example, such boron compounds are useful as neutron capture therapy agents when employed in boron neutron capture therapy (BNCT).

BACKGROUND ART

Recently, attention has been drawn to a boron neutron capture therapy (BNCT) as a novel cancer therapeutic method utilizing a radioisotope. The boron neutron capture therapy is a therapeutic method in which a boron compound containing boron-10 isotope ($^{10}B$) is delivered to cancer cells and the cancer cells are irradiated with a low energy neutron (for example, thermal neutrons), and thus the cancer cells are locally destroyed by a nuclear reaction which arises in the cells. In this therapeutic method, since it is important to cause boron compound(s) which contain $^{10}B$ to be selectively accumulated by cells of cancerous tissue so as to enhance therapeutic effect, boron compounds which are selectively uptaken by cancer cells have been developed.

Hitherto, some boron-containing compounds in which boron atoms or boron atomic groups are introduced into a basic skeleton have been synthesized as an agent used in BNCT. Examples of such an agent used in the actual clinical practice include p-boronophenylalanine (BPA) and mercaptoundecahydro-dodecaborate (BSH: borocaptate). Among these agents, BSH is a boron cage (cluster) compound having the lowest toxicity, which is mainly used in the form of a sodium salt for the treatment of brain tumor, and thus utility thereof has been confirmed (see, for example, Non-Patent Documents 1 to 8).

PRIOR ART DOCUMENTS

Non-Patent Document

Non-Patent Document 1: I. M. Wyzlic et al., Tetrahedron Lett., 1992, 33, 7489-7490;
Non-Patent Document 2: W. Tjark, J. Organomet. Chem., 2000, 614-615, 37-47;
Non-Patent Document 3: K. Imamura et al., Bull. Chem. Soc. Jpn., 1997, 70. 3103-3110;
Non-Patent Document 4: A. S. Al-Madhorn et al., J. Med. Chem., 2002, 45, 4018-4028;
Non-Patent Document 5: F. Compostella et al., Res. Develop. Neutron Capture Ther., 2002, 81-84;
Non-Patent Document 6: S. B Kahl et al., Progress in Neutron Capture Therapy for Cancer, Plenum Press, New York 1992, 223;
Non-Patent Document 7: J. Cai et al., J. Med. Chem., 1997, 40, 3887-3896;
Non-Patent Document 8: H. Lim et al., Res. Develop. Neutron Capture Ther., 2002, 37-42

SUMMARY OF THE INVENTION

Problems to be Solved by the Invention

As described above, it has been desired to develop a novel boron-containing compound which is selectively uptaken by cancer cells and which may be used to carry out BNCT.

The objective of the present invention is to provide a novel boron-containing compound and a method for producing the same, which can be utilized for BNCT and the like.

Means for Solving the Problems

The present inventors have intensively studied and, as a result, have found that the above objective can be achieved by a boron compound having an amino acid skeleton containing a cyclo-type ring and a method for producing the same as shown below, and thus the present invention has been completed.

That is, the present invention relates to a boron compound having an amino acid skeleton containing a cyclo-type ring, represented by the general formula (I):

wherein l is an integer of 1 to 6; m is 0, 1 or 2; and n is 0, 1 or 2; or a pharmaceutically acceptable salt thereof.

In the present invention, a boron compound is defined as below.

In the boron compound having an amino acid skeleton containing a cyclo-type ring above, l may be 1, m may be 0 or 1, and n may be 0 or 1.

The present invention further relates to the boron compound having an amino acid skeleton containing a cyclo-type ring, which is represented by the general formula (II):

wherein l represents an integer of 1 to 6; or a pharmaceutically acceptable salt thereof.

The present invention further relates to a boron compound having an amino acid skeleton containing a cyclo-type ring, which is represented by the general formula (III):

(III)

wherein l represents an integer of 1 to 6; or a pharmaceutically acceptable salt thereof.

The present invention further relates to a method for producing a boron compound having an amino acid skeleton containing a cyclo-type ring, the method comprising the step of reacting a cyanoethyl BSH (1) represented by the general formula (1):

(1)

with a compound (2) represented by the general formula (2):

(2)

wherein X is a halogen, l represents an integer of 1 to 6, m is 0, 1, or 2, and n is 0, 1, or 2, in the presence of an alkali.

The present invention further relates to a method for producing a boron compound having an amino acid skeleton containing a cyclo-type ring, the method comprising the step of reacting a cyanoethyl BSH (1) represented by the general formula (1) with a compound (3) represented by the general formula (3):

(3)

wherein X is a halogen, l represents an integer of 1 to 6, m is 0, 1, or 2, and n is 0, 1, or 2, in the presence of an alkali.

According to the present method, a boron compound having an amino acid skeleton containing a cyclo-type ring represented by the general formula (1) can be prepared.

Effect of the Invention

Since a boron compound (I) having an amino acid skeleton containing a cyclo-type ring in accordance with the present invention has a hydrophobic portion as well as an amino acid skeleton, it is a novel substance which can be conveniently delivered to cancer cells through use of cancer-specific essential amino acid transporter(s) (LAT1). Therefore, the boron compound having an amino acid skeleton containing a cyclo-type ring of the present invention is particularly useful in BNCT which targets cancer cells.

MODE FOR CARRYING OUT THE INVENTION

Below, description is given with respect to the boron compound having an amino acid skeleton containing a cyclo-type ring in accordance with the present invention, represented by the following general formula (I) and pharmaceutically acceptable salts thereof.

In the general formula (I):

(I)

In the formula, l represents an integer of 1 to 6; m is 0, 1 or 2; and n is 0, 1, or 2.

In the boron compound having an amino acid skeleton containing a cyclo-type ring, preferred is a compound where l is 1, m is 0 or 1, and n is 0 or 1, or a pharmaceutically acceptable salt thereof.

Among them, a boron compound having an amino acid skeleton containing a cyclo-type ring, represented by the general formula (II):

(II)

wherein l represents an integer of 1 to 6, or a pharmaceutically acceptable salt thereof is especially preferable.

Alternatively, a boron compound having an amino acid skeleton containing a cyclo-type ring, represented by the general formula (III):

(III)

is preferable.

A boron compound having an amino acid skeleton containing a cyclo-type ring in accordance with the present invention, represented by:

is more preferable, or a boron compound having an amino acid skeleton containing a cyclo-type ring, represented by:

is most preferable.

Hereinafter, methods for producing a boron compound having an amino acid skeleton containing a cyclo-type ring represented by the general formula (I) described above will be explained.

In a method for producing a boron compound having an amino acid skeleton containing a cyclo-type ring in accordance with the present invention, a cyanoethyl BSH represented by the general formula (1) is used as starting material:

These BSH compounds can be synthesized, but not limited to, according to the method known from the literatures (for example, Gabel, D.; Moller, D.; Harfst, S.; Rosler, J.; Ketz, H.; Inorg. Chem. 1993, 32, 2276-2278). That is, this method comprises reacting BSH and β-bromopropionitrile in acetonitrile, and then treating the product with tetramethyl ammonium hydroxide and the like, thereby to obtain a desired cyanoethyl BSH compound.

Here, the BSH is a compound having an icosahedral boron cluster structure including boron, hydrogen, and sulfur atoms. BSH, having a so-called three-center bond structure in which three boron atoms have two electrons in common, has a specific structure in which electrons are localized, and has a volume that is larger than that of a benzene ring despite the fact that the BSH is an inorganic compound of low molecular weight.

A boron compound having an amino acid skeleton containing a cyclo-type ring in accordance with the present invention can be produced by reacting such a cyanoethyl BSH (1) with a compound represented by the general formula (2):

(2)

wherein X is a halogen; l is an integer of 1 to 6; m is 0, 1 or 2; and n is 0, 1 or 2, in the presence of an alkali.

Also, a boron compound having an amino acid skeleton containing a cyclo-type ring in accordance with the present invention can be obtained by the reaction of a cyanoethyl BSH (1) represented by the general formula (1) with a compound (3) represented by the general formula (3):

(3)

wherein X is a halogen; l is an integer of 1 to 6; m is 0, 1 or 2; and n is 0, 1 or 2, in the presence of an alkali, followed by reflux in the presence of an alkali.

Here, the production method of the compound represented by the chemical formula (2) or (3) is not limited, and one example of a synthetic route is shown using a compound having, for example, a cyclobutane ring.

In the above formulae, Bn is a benzyl group. First, copper (II) acetate monohydrate is dissolved in acetic acid, zinc powder is added to this solution, and allyl benzyl ether dissolved in dry diethyl ether was added thereto. Trichloroacetyl chloride and phosphoryl trichloride dissolved in dry diethyl ether are added dropwise to the solution. The reaction solution is refluxed, stirred, returned to room temperature, and filtered. The filtrate is washed, dehydrated, concentrated, and then to the residue are added acetic acid and zinc powder, followed by stirring under reflux. After the reaction solution is filtered, the filtrate is concentrated, the residue is dissolved in ethyl acetate, and zinc powder precipitated upon neutralization is filtered off. This filtrate is separated, washed with saturated $NaHCO_3$ solution and brine, and the organic phase is dehydrated, concentrated, and evaporated under reduced pressure to remove the unreacted allyl benzyl ether, thereby to obtain 3-(benzyloxymethyl)cyclobutanone.

Next, using 3-(benzyloxymethyl)cyclobutanone thus obtained, cis- and trans-hydantoins containing benzyloxymethylcyclobutane moiety can be produced.

The thus obtained cis- or trans-hydantoin containing benzyloxymethylcyclobutane moiety is reacted with an alkali solution, and after addition of a conc. hydrogen halide solution, the mixture can be refluxed to obtain, for example, cis- or trans-1-amino-3-(bromomethyl)cyclobutanecarboxylic acid hydrobromide.

Then, the cis- or trans-hydantoins containing the benzyloxymethylcyclobutane moiety can be converted into a halogenated hydantoin.

Further, as an alternative method for producing the compound represented by the chemical formula (2) or (3), a synthetic route where a compound having a cyclobutane ring, cyclohexane ring, or other such cyclo-type ring may be produced is shown.

Ethyl 4-cyclohexanocarboxylate, ethylene glycol, and p-toluenesulfonic acid monohydrate are dissolved in toluene, and then refluxed using a Dean-Stark apparatus. After completion of the reaction, the reaction solution is concentrated under reduced pressure, and 5% aqueous sodium hydrogen carbonate solution is added thereto. Further, this mixture is extracted with ether, and, after drying the extracted ether layer over sodium sulfate, it is concentrated under reduced pressure. Then the residue is purified by silica gel column chromatography to obtain a dioxolane intermediate.

After suspending LiAlH$_4$ in anhydrous THF, the dioxolane intermediate obtained above is added dropwise thereto. After further reflux, a saturated aqueous sodium hydrogen carbonate solution is added dropwise slowly to the mixture at room temperature. The mixture is filtered through Celite and the filtrate is concentrated under reduced pressure. The residue is dissolved in ethyl acetate and the ethyl acetate layer is washed with a saturated aqueous sodium hydrogen carbonate solution and further brine, dried over sodium sulfate, and concentrated under reduced pressure to obtain a desired alcohol intermediate.

At 0° C., 60% NaH is added to the alcohol intermediate dissolved in THF. After stirring the mixture, benzyl bromide is added thereto and the mixture is stirred at room temperature for 18 hours. Then, the reaction solution is neutralized with an aqueous 1N hydrochloric acid solution and concentrated under reduced pressure. Subsequently, the residue is dissolved in ether and the resulting solution is washed with water and brine, and the solvent is concentrated under reduced pressure. The residue is then purified by silica gel column chromatography to obtain a desired ether intermediate.

The ether intermediate is dissolved in an aqueous 1N hydrochloric acid solution, and the solution is stirred at room temperature for 1 hour, after which time the reaction solution is washed with chloroform and neutralized with sodium carbonate. After extraction of the neutralized solution with ethyl acetate, the organic layer is dried over sodium sulfate and concentrated under reduced pressure to obtain a desired ketone intermediate.

Then, the benzyloxyketone intermediate is halogenated.

In each step, a subsequent step may be done after appropriate neutralization and purification steps have been applied.

Each product obtained in the each step may be isolated and purified, or may be subjected to the subsequent step as it is. The isolation and purification means include washing, extraction, recrystallization methods, various chromatographies and the like. In each product in the each step, these isolation and purification means can also be used alone, or in appropriate combination of two or more kinds of them.

Such a compound can be suitably used as it is, or used in the form of a pharmaceutically acceptable salt, or used in the form of a pharmaceutical preparation known to a person with an ordinary skill in the art by mixing it with a pharmaceutically acceptable carrier, or used in the form of a BSH-enclosed viral envelope vector and the like in a boron neutron capture therapy (BNCT). Examples of the pharmaceutically acceptable salt include salts with an inorganic base, salts with an organic base, salts with an inorganic acid, salts with an organic acid, salts with a basic or acidic amino acid and the like. Preferred examples of the salts with an inorganic base include, for example, alkali metal salts such as a sodium salt and a potassium salt; alkaline earth metal salts such as a calcium salt and a magnesium salt; an aluminum salt, an ammonium salt and the like. Preferred examples of the salts with an organic base include, for example, salts with trimethylamine, triethylamine, pyridine, picoline, ethanolamine, diethanolamine, triethanolamine, dicyclohexylamine, N,N'-dibenzylethylenediamine and the like. Preferred examples of the salts with an inorganic acid include, for example, salts with hydrochloric acid, hydrobromic acid, nitric acid, sulfuric acid, phosphoric acid and the like. Preferred examples of the salts with an organic acid include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferred examples of the salts with a basic amino acid include, for example, salts with arginine, lysine, ornithine and the like, and preferred examples of the salts with an acidic amino acid include, for example, salts with aspartic acid, glutamic acid and the like.

The treatment is performed via any appropriate route of administration by administering an agent containing a compound in accordance with the present invention using a method in which the compound is accumulated at the target site. The compound of the present invention is preferably concentrated in tumor. The pharmaceutical preparation containing the compound can be administered at a time, or can be sequentially administered. Administration of the pharmaceutical preparation can be optionally repeated. If desired, after removing the tumor to a surgically possible extent, the remaining tumor can also be destroyed using a pharmaceutical preparation in accordance with the present invention.

A treatment using the pharmaceutical preparation of the BSH derivative in accordance with the present invention is performed via any appropriate route of administration by administering it using a method in which a BSH derivative is accumulated in the target tumor. The BSH derivative is preferably concentrated to the tumor before irradiation with radiation. A tumor/blood ratio before irradiation with radiation is advantageously about 2:1 or at least 1.5:1. The BSH derivative can be administered at a time, or can be sequentially administered. After the compound is desirably accumulated in the tumor, the site is irradiated with an effective amount of low energy neutrons. The site can be irradiated through the skin, or the site can be completely or partially exposed before irradiation. Administration of the BSH derivative and the subsequent irradiation with radiation can be repeated as needed. If desired, after removing the tumor to a surgically possible extent, the remaining tumor is destroyed using a BSH derivative in accordance with the present invention. In another aspect, a proper amount of the BSH derivative may be administered to patients, followed by irradiation with an effective amount of $^{252}$californium which is a naturally occurring neutron radiation substance. It is preferred that $^{252}$californium is inserted into the tumor and then removed within a proper time.

In order to administer a BSH derivative in accordance with the present invention, the BSH derivative may be administered to patients by mixing with proper excipients, adjuvants and/or pharmaceutically acceptable carriers, alone or in combination with other agents. The carriers which can be particularly preferably used include, but are not limited to, physiological saline, buffered physiological saline, dextrose, water, and the like. In an embodiment of the present invention, the pharmaceutically acceptable carriers are pharmaceutically inactive.

A BSH derivative in accordance with the present invention may be administered orally and parenterally. In the case of parenteral administration, the BSH derivative may be administered intraarterially (for example, via carotid artery), intramuscularly, subcutaneously, intramedullary, intrathecally, intraventricularly, intravenously, intraperitoneally, or intranasally.

The pharmaceutical preparation may be formulated into any form such as powders, granules, fine granules, dry syrups, tablets, capsules, injections, and liquids and solutions. In addition, depending on the dosage form, the pharmaceutical preparation can be prepared by appropriately mixing with, or diluting and dissolving together with pharmaceutical additives, for example, proper excipients; disintegrators; binders; lubricants; diluents; buffers such as phosphoric acid, citric acid, succinic acid, acetic acid and other organic acids, or salts thereof; isotonizing agents; antiseptics; humectants; emulsifiers; dispersing agents; stabilizers; solubilizers; antioxidants such as ascorbic acid; low molecular (less than about 10 residues) polypeptides (for example, polyarginine or tripeptides); proteins (for example, serum albumin, gelatin, or immunoglobulin); hydrophilic polymers (for example, polyvinylpyrrolidone); amino acids (for example, glycine, glutamic acid, aspartic acid, or arginine); monosaccharides, disaccharides and other carbohydrates (including cellulose or derivatives thereof, glucose, mannose, or dextrin); chelating agents (for example, EDTA); sugar alcohols (for example, mannitol or sorbitol); counter ions (for example, sodium); and/or nonionic surfactants (for example, polysorbate, poloxamer) according to the pharmaceutically known techniques. Such a substance, which enhances isotonicity and chemical stability, is nontoxic to the recipient at the dosages and concentrations used.

Techniques for formulation and administration are described, for example, in the latest edition of the Japanese Pharmacopoeia and its latest supplement, and in the final version of "REMINGTON'S PHARMACEUTICAL SCIENCES" (Maack Publishing Co., Easton, Pa.).

A pharmaceutical preparation of a BSH derivative in accordance with the present invention is a pharmaceutical agent which contains the desired agent in an amount effective to achieve the intended purpose, and the "therapeutically effective amount" or "pharmacologically effective amount" is well recognized by a person ordinarily skilled in the art, and refers to an amount of an agent effective to produce a pharmacological result. Determination of the therapeutically effective amount is well known to a person ordinarily skilled in the art.

The therapeutically effective amount refers to an amount of the agent to alleviate the disease state by the administration. The therapeutic effect and toxicity of such compounds may be determined by standard pharmaceutical procedures in cell cultures or experimental animals. The dose is preferably in the range of circulating concentrations that include the $ED_{50}$ with little or no toxicity. This dose varies within this range depending on the dosage form used, sensitivity of patients, and administration route. As an example, the dose of a composite is appropriately chosen depending on the age or other conditions of patients, the kind of diseases, the kind of composites to be used and the like. Preferred daily dose of the compound of the formula (I) is 0.01 to 1,000 mg per 1 kg of the weight of the mammal to be treated. In humans, the preferred daily dose of the compound of the formula (1) is 0.01 to 800 mg, more preferably 1 to 600 mg, per 1 kg of the weight.

Hereinafter, specific examples of a boron compound having an amino acid skeleton containing a cyclo-type ring in accordance with the present invention will be described by way of aspects of Examples, but the present invention should not be construed as being limited thereto.

EXAMPLES

In the following examples, analysis and isolation/purification of compounds were performed using the following models and reagents.

NMR spectrum: JEOL JMTC-400/54/SS 400 MHz (manufactured by JEOL, Ltd.). Unless otherwise specified, TMS was used as an internal standard. The following chemical shift was expressed by the δ value.

Silica gel for column chromatography: BW-200 (manufactured by FUJI SILYSIA CHEMICAL LTD.)

Melting point was measured by using a BUCHI melting point B-545 apparatus.

IR was measured by using a JASCO FT/IR-460 plus spectrometer.

Example 1

Production of 3-(benzyloxymethyl)cyclobutanone

Into a 200 ml four-necked flask, copper(II) acetate monohydrate (0.16 g) was added and dissolved in 5 ml of acetic acid. Zinc powder (2.8 g) was added to this solution, and after allowing the mixture to stir for 90 seconds, decantation was carried out. Acetic acid (1 ml) was added to the residue and decantation was repeated five times. Dry diethyl ether (6 ml) was added to the residue and decantation was repeated three times. The atmosphere in the reaction vessel was completely replaced with argon gas by operating a three-way stopcock that was connected to an aspirator. Allyl benzyl ether 6.3 g (6.3 ml, 40.5 mmol) dissolved in 60 ml of dry diethyl ether was placed in this reaction vessel. Trichloroacetyl chloride 5.0 ml (45 mmol) and phosphoryl trichloride 4.1 ml (45 mmol) that were dissolved in 40 ml of dry diethyl ether were added dropwise to the above solution over a period of one hour. This reaction solution was refluxed and stirred for 21 hours. After the reaction solution was returned to room temperature, it was filtered. The filtrate was quenched by the addition of water and washed with water and brine. The organic layer was dehydrated over anhydrous sodium sulfate and then concentrated. Acetic acid (33 ml) and zinc powder (13.3 g) were added to the residue, and the mixture was stirred under reflux for 4 hours. This reaction solution was filtered and the filtrate was concentrated. This residue was dissolved in ethyl acetate, and zinc powder precipitated upon neutralization with a saturated $NaHCO_3$ solution was separated by filtration using Celite. The filtrate was separated into two layers and washed with a saturated $NaHCO_3$ solution and brine. The organic layer was dehydrated over sodium sulfate and then concentrated. The unreacted allyl benzyl ether was removed by evaporation under reduced pressure in a glass tube oven. The residue was purified by silica gel chromatography (toluene:ethyl acetate=96:4) to obtain 3-(benzyloxymethyl)cyclobutanone (2.41 g, 29%) as a clear oil. A clear oil: b.p. 115° C./1.0 mmHg. (TLC; Rf=0.20 (G):(M))

($^1$H-NMR ($CD_3Cl$); 2.68 (1H, m, $BnOCH_2CH$—), 2.86 (2H, m, —$CH_aH_bCOCH_aH_b$—), 3.11 (2H, m, —$CH_aH_bCOCH_aH_b$—), 3.57 (2H, d, J=6.3 Hz, $BnOCH_2$—), 4.53 (2H, s, $PhCH_2$—), 7.32 (5H, m, $C_6H_5$—))

($^{13}$C-NMR ($CDCl_3$); 23.6, 49.9, 72.8, 73.1, 127.6, 128.4, 138.0, 207.4)

Production of 3-(benzyloxymethyl)cyclobutanone hydantoin 3-(Benzyloxymethyl)cyclobutanone 4.0 g (21 mmol), sodium cyanide 2.1 g (42 mmol) and ammonium carbonate 10.1 g (105 mmol) were added into a 100-ml eggplant-shaped flask, and the mixture was dissolved in 50 ml of 50% water/ethanol. This eggplant-shaped flask was sealed and the mixture was stirred overnight at 60° C. After opening this flask with caution in a draft chamber, the reaction solution was concentrated under reduced pressure. The residue was dissolved in ethyl acetate and filtered to remove insoluble inorganic salts. The filtrate was concentrated under reduced pressure and the residue was purified by silica gel chromatography (hexane:ethyl acetate=50:50). Thus, 3-(benzyloxymethyl)cyclobutanone hydantoin was obtained as a white crystal (cis-form 2.8 g, 11 mmol, 50%; trans-form 1.1 g, 4.3 mmol, 21%).

Cis-Form: White Crystal (TLC; Rf=0.28 (D):(N))

($^1$H-NMR ($CD_3Cl$); 2.23 (2H, dd, J=6.3 Hz, 13 Hz, —$CH_aH_bC(NHCONHCO)$ $CH_aH_b$—), 2.58 (1H, m, $BnOCH_2CH$—), 2.77 (2H, dd, J=9.1 Hz, 13 Hz, —$CH_aH_bC(NHCONHCO)CH_aH_b$—), 3.48 (2H, d, J=3.7 Hz, $BnOCH_2$—), 4.58 (2H, s, $PhCH_2$—), 6.06 (1H, b, —$CH_2NHCO$—), 7.35 (5H, m, $C_6H_5$—), 7.74 (1H, b, —CONHCO—))

Trans-Form: White Crystal (TLC; Rf=0.28 (D):(N))

($^1$H-NMR ($CD_3Cl$); 2.41 (2H, m, —$CH_aH_bCOCH_aH_b$—), 2.52 (2H, m, —$CH_aH_bCOCH_aH_b$—), 2.67 (1H, m, $BnOCH_2CH$—), 3.66 (2H, d, J=7.3 Hz, $BnOCH_2$—), 4.54 (2H, s, $PhCH_2$—), 6.17 (1H, b, —$CH_2NHCO$—), 7.33 (5H, m, $C_6H_5$—), 7.88 (1H, b, —CONHCO—))

Production of cis-1-amino-3-(bromomethyl)cyclobutane-carboxylic acid hydrobromide

500 mg (1.92 mmol) of 3-(benzyloxymethyl)cyclobutanone cis-hydantoin and 20 ml of 0.5 N NaOH were added into a 50-ml eggplant-shaped flask, and the mixture was stirred at 60° C. for 24 hours. The reaction solution was concentrated, a concentrated aqueous HBr solution 15 ml was added thereto, and the mixture was stirred under reflux for 6 hours, after which time the reaction solution was concentrated under reduced pressure. This residue was dissolved in water and the insoluble materials were removed by filtration. The filtrate was concentrated under reduced pressure and the residue was dissolved in acetonitrile to remove the insoluble materials by filtration. The residue obtained by concentrating the filtrate under reduced pressure was purified by reverse phase silica gel chromatography to obtain cis-1-amino-3-(bromomethyl)cyclobutanecarboxylic acid hydrobromide (64.5 mg, 0.22 mmol, 12%) as a white crystal.

While Crystal (TLC; Rf=0.52 (C):(N))

($^1$H-NMR ($D_wO$); 2.11 (2H, m, —$CH_aH_bC${($NH_2$—HBr)($CO_2H$)}$CH_aH_b$—), 2.62 (2H, m, —$CH_aH_bC${($NH_2$—HBr)($CO_2H$)}$CH_aH_b$—), 2.86 (1H, m, $BrCH_2CH$—), 3.43 (2H, m, $BrCH_2$—))

Production of cis-1-amino-3-(dodecaboranylthiomethyl)cyclobutanecarboxylic acid hydrobromide ditetramethylammonium Cis-1-amino-3-(bromomethyl)cyclobutanecarboxylic acid hydrobromide (63 mg, 0.22 mmol), dodecaboranyl-(β-cyano)ethyl}sulfide tetramethylammonium salt (0.20 mg, 0.20 mmol), and dry acetonitrile (5 ml) were added to a 25-ml three-necked flask, and the mixture was stirred under reflux in an inert gas overnight. After concentration of the solution under reduced pressure, acetone was added to the residue. The acetone-insoluble solid was separated by filtration and the filtrate was concentrated under reduced pressure. To the residue were added acetone (20 ml) and 40% methylaminemethanol solution (0.52 ml), and the mixture was stirred under ice-cooling. Then, a 10% solution of tetramethylammonium hydroxide in methanol (0.23 ml, 0.21 mmol) was added, and the mixture was stirred for 30 minutes, after which time the reaction solution was concentrated under reduced pressure. Acetone was added to the residue to collect an acetone-insoluble solid by filtration. The solid obtained by this filtration was dissolved in pure water, passed through a glass column packed with Amberlite IR 120 cation-exchange resin (H+ form) (manufactured by Rohm and Hass Co.), and the aqueous eluate was concentrated under reduced pressure. The residue was dissolved in a small amount of pure water and after addition of a 10% solution (0.45 ml, 0.41 mmol) of tetramethylammonium hydroxide in methanol thereto, the mixture was concentrated under reduced pressure. The residue was purified by reverse phase column chromatography on silica gel to obtain a compound (51 mg, 0.099 mmol, 49%) as a white crystal.

White Crystal (TLC; Rf=0.31 (C):(N,I))

($^1$H-NMR (D$_2$O); 0.75-1.80 (11H, m, —B$_{12}$H$_{11}$), 2.10 (2H, m, —CH$_a$H$_b$C {(NH$_2$—HBr)(CO$_2$H)}CH$_a$H$_b$—), 2.66 (5H, m, B$_{12}$H$_{11}$SCH$_2$—, —CH$_a$H$_b$C {(NH$_2$—HBr)(CO$_2$H)}CH$_a$H$_b$—), 3.22 (24H, s, —N(CH$_3$)$_4$))

(IR(KBr); 3570, 3411, 3210, 3023, 2491, 2032, 1878, 1618, 1486, 1400, 1268, 1071, 993)

(MS (ESI): m/z 514.6[M+3NMe$_4$]$^{1+}$, $^{440.5}$[M+2NMe$_4$+H]$^{1+}$, 366.2 [M+NMe$_4$]$^{1-}$ 132.2 [B$_{12}$H$_{11}$]$^{1-}$)

Example 2

Production of 3-(hydroxymethyl)cyclobutanone cis-hydantoin

3-(Benzyloxymethyl)cyclobutanone cis-hydantoin 1.2 g (4.6 mmol) was dissolved in 30 ml of methanol. To this solution was added 240 mg of 20% Pd(OH$_2$) under ice cooling. The reaction solution was stirred overnight at room temperature under a hydrogen atmosphere of 5.5 atm. After confirming the progress of the reaction by TLC, the 20% Pd(OH)$_2$ was filtered off with a filter paper and Celite. The filtrate was concentrated to obtain 3-(hydroxymethyl)cyclobutanone cis-hydantoin (770 mg, 4.5 mmol, 98%) as a white solid.

White Crystal (TLC; Rf=0.18 (H):(N))

($^1$H-NMR (CD$_3$OD); 2.13 (2H, m, —CH$_a$Hb$_c$(NHCONHCO)CH$_a$H$_b$—), 2.51 (3H, m, BnOCHCH$_a$H$_b$C(NHCONHCO)CH$_a$H$_b$—), 3.37 (1H, b, HOCH$_2$—), 3.51 (2H, d, J=5.1 Hz))

Production of 3-(iodomethyl)cyclobutanone cis-hydantoin

1.15 g (9.06 mmol) of iodine and 617 mg (9.06 mmol) of imidazole were dissolved in 10 ml of dry dichloromethane. 2.38 g (9.06 mmol) of triphenylphosphine was added thereto under ice cooling and the mixture was stirred for 30 minutes. Then, the temperature was raised to room temperature over one hour. After addition of 770 mg (4.5 mmol) of 3-(hydroxymethyl)cyclobutanone cis-hydantoin and 10 ml of dry dichloromethane thereto, the mixture was stirred at room temperature for 5 hours. After completion of the reaction, the white solid precipitated was collected by filtration and washed with chloroform. The filtered solid was dissolved in ethyl acetate and the solution was washed with 1N HCl and brine. The organic layer was dehydrated over sodium sulfate, filtered, and the filtrate was concentrated under reduced pressure to obtain a white solid of 3-(iodomethyl)cyclobutanone cis-hydantoin (506 mg, 1.80 mmol, 40%) as a crude product.

White Crystal (TLC; Rf=0.60 (G):(N))

($^1$H-NMR (CD$_3$OD); 1.98 (2H, m, —CH$_a$H$_b$C(NHCONHCO)CH$_a$H$_b$—), 2.56 (2H, m, —CH$_a$H$_b$C(NHCONHCO)CH$_a$H$_b$—), 2.68 (1H, m, ICH$_2$CH—), 3.38 (1H, m, ICH$_2$—)

Production of 3-(dodecaboranylthiomethyl)cyclobutanone ditetramethylammonium salt

543 mg (1.49 mmol) of dodecaboranyl-{(2-cyano) ethyl}sulfide ditetramethylammonium salt, 500 mg (1.79 mmol) of 3-(iodomethyl)cyclobutanone cis-hydantoin, and a total of 20 ml of dry acetonitrile were added to a 50-ml two-necked flask. The reaction solution was stirred overnight under reflux and concentrated under reduced pressure after confirmation of the completion of the reaction by TLC. The residue was added to acetone to remove insoluble materials by filtration. The residue was dissolved in a minimum amount of acetone at room temperature. To this solution was gradually added a 10% methanol solution 1.7 ml (1.56 mmol) of tetramethylammonium hydroxide, and the mixture was stirred for 30 minutes. The reaction solution was concentrated under reduced pressure. Acetone was added to the residue to collect the insoluble material by filtration. This filtered insoluble material was dissolved in pure water and washed with ethyl acetate. The aqueous layer was passed through HP20 and the eluate was concentrated under reduced pressure. The residue was recrystallized from pure water to obtain 3-(dodecaboranylthiomethyl)cyclobutanone ditetramethylammonium salt (414 mg) as a white crystal. The filtrate was also concentrated under reduced pressure. The residue was purified by reverse phase chromatography on silica gel to obtain 149 mg (563 mg in total, 1.21 mmol, 81%)) of 3-(dodecaboranylthiomethyl)cyclobutanone ditetramethylammonium salt as a white crystal.

(TLC; Rf=0.47 (C):(N,I))

($^1$H-NMR (D$_2$O); 0.75-1.60 (11H, m, —B$_{12}$H$_{11}$), 1.94 (2H, t, J=10.7 Hz, —CH$_a$H$_b$C(NHCONHCO)CH$_a$H$_b$—), 2.34 (1H, m, B$_{12}$H$_{11}$SCH$_2$CH—), 2.46 (4H, m, B$_{12}$H$_{11}$SCH$_2$—, —CH$_a$H$_b$C(NHCONHCO)CH$_a$H$_b$—), 3.00 (24H, s, —N(CH$_3$)$_4$))

(IR(KBr); 3586, 3363, 3183, 3077, 3031, 2975, 2932, 2842, 2766, 2494, 2028, 1766, 1719, 1485, 1402, 1311, 1143, 1070)

Production of cis-1-amino-3-(dodecaboranylthiomethyl)cyclobutanecarboxylic acid trisodium salt

40 mg (0.086 mmol) of 3-(dodecaboranylthiomethyl)cyclobutanone ditetramethylammonium salt and 3.4 ml of 0.5 N NaOH were added to a 10-ml eggplant-shaped flask, and the mixture was stirred overnight under reflux. After confirmation of the progress of the reaction by TLC, the reaction solution was passed through Amberlite IR 120B cation-exchange resin (H$^+$ form) and the eluate was concentrated under reduced pressure. The residue was dissolved in water and passed through a membrane filter of PTFE. The filtrate was passed through Amberlite IR 120B cation-exchange resin (Na$^+$ form) and the eluate was concentrated under reduced pressure to obtain cis-1-amino-3-(dodecaboranylthiomethyl) cyclobutane-carboxylic acid trisodium salt (31 mg, quant.) as a white solid.

(TLC; Rf=0.31 (C):(N,I))

($^1$H-NMR (D$_2$O); 0.75-1.90 (11H, m, —B$_{12}$H$_{11}$), 2.06 (2H, m, —CH$_a$H$_b$C{(NH$_2$—HBr)(CO$_2$H)}CH$_a$H$_b$—), 2.62 (5H, m, B$_{12}$H$_{11}$SCH$_2$—, —CH$_a$H$_b$C{(NH$_2$—HBr)(CO$_2$H)}CH$_a$H$_b$—), 3.22 (24H, s, —N(CH$_3$)$_4$))

Example 3

Production of 3-(hydroxymethyl)cyclobutanone trans-hydantoin

3-(Benzyloxymethyl)cyclobutanone trans-hydantoin 1.2 g (4.6 mmol) was dissolved in 30 ml of methanol. To this solution was added 240 mg of 20% Pd(OH$_2$) under ice cooling. The reaction solution was stirred overnight at room temperature under a hydrogen atmosphere of 5.5 atm. After confirming the progress of the reaction by TLC, the 20% Pd(OH$_2$) was filtered off with a filter paper and Celite. The filtrate was concentrated to obtain 3-(hydroxymethyl)cyclobutanone trans-hydantoin (770 mg, 4.5 mmol, 98%) as a white solid.

White Crystal (TLC; Rf=0.20 (H):(N))

($^1$H-NMR (CD$_3$OD); 2.36 (4H, m, —CH$_2$C(NHCONHCO)CH$_2$—), 2.55 (1H, m, HOCH$_2$CH—), 3.70 (1H, d, HOCH$_2$—))

Production of 3-(iodomethyl)cyclobutanone trans-hydantoin 744 mg (5.86 mmol) of iodine and 399 mg (5.86 mmol) of imidazole were dissolved in 5 ml of dry dichloromethane. 1.54 g (5.86 mmol) of triphenylphosphine was added thereto under ice cooling and the mixture was stirred for 30 minutes. Then, the temperature was raised to room temperature over one hour. After addition of 498 mg (2.93 mmol) of 3-(hydroxymethyl)cyclobutanone trans-hydantoin and 5 ml of dry dichloromethane thereto, the mixture was stirred at room temperature for 5 hours. The reaction solution was concentrated and washed with hexane. The residue was dissolved in ethyl acetate and then filtered. The filtrate was washed with 1N HCl and brine. The organic layer was dehydrated over sodium sulfate, filtered, and the filtrate was concentrated under reduced pressure. The residue was purified by silica gel chromatography (hexane:ethyl acetate=40:60), thereby to obtain a white solid of 3-(iodomethyl)cyclobutanone trans-hydantoin (406 mg, 1.45 mmol, 49%) as a crude product.

(TLC; Rf=0.59 (G):(N))

Production of 3-(dodecaboranylthiomethyl)cyclobutanone ditetramethylammonium salt trans-hydantoin 430 mg (1.18 mmol) of dodecaboranyl-{(2-cyano) ethyl}sulfide ditetramethyl-ammonium salt, 494 mg (1.77 mmol) of 3-(iodomethyl)cyclobutanone trans-hydantoin, and 10 ml of dry acetonitrile were added to a 30-ml two-necked flask. The reaction solution was stirred overnight under reflux. After confirmation of the completion of the reaction by TLC, the reaction solution was concentrated under reduced pressure. The residue was added to acetone to remove insoluble materials by filtration. The residue was dissolved in a minimum amount of acetone at room temperature. To this solution was gradually added a 10% methanol solution 1.34 ml (1.25 mmol) of tetramethylammonium hydroxide, and the mixture was stirred for minutes. The reaction solution was concentrated under reduced pressure. Acetone was added to the residue to collect the insoluble material by filtration. This insoluble material was dissolved in water, passed through HP20, IR120 ($H^+$ form) and IR120 ($Na^+$ form), and the eluate was concentrated under reduced pressure. The residue was purified by reverse phase silica gel chromatography to obtain 3-(dodecaboranylthiomethyl)cyclobutanone ditetramethylammonium salt trans-hydantoin (150 mg in total, 0.32 mmol, 37%) as a clear oil.

(TLC; Rf=0.44 (C):(N,I))

($^1$H-NMR ($D_2O$); 0.75-1.60 (11H, m, —$B_{12}H_{11}$), 2.11 (2H, m, —$CH_aH_bC(NHCONHCO)CH_aH_b$—), 2.22 (2H, m, —$CH_aH_bC(NHCONHCO)CH_aH_b$—), 2.59 (3H, m, $B_{12}H_{11}SCH_2CH$—))

Production of trans-1-amino-3-(dodecaboranylthiomethyl)cyclobutanecarboxylic acid trisodium salt 54.3 mg (0.157 mmol) of 3-(dodecaboranylthiomethyl) cyclobutanone disodium salt trans-hydantoin and 6.0 ml of 0.5 N NaOH were added to a 20-ml eggplant-shaped flask, and the mixture was stirred overnight under reflux. After confirmation of the progress of the reaction by TLC, the reaction solution was passed through Amberlite IR 120B cation-exchange resin ($H^+$ form) and the eluate was concentrated under reduced pressure. The residue was dissolved in water and passed through a membrane filter of PTFE. The filtrate was passed through Amberlite IR 120B cation-exchange resin ($Na^+$ form) and the eluate was concentrated under reduced pressure. The residue was purified by reverse phase chromatography on silica gel to obtain trans-1-amino-3-(dodecaboranylthiomethyl)cyclobutanecarboxylic acid trisodium salt (47.7 mg, 84%) as a white solid.

(TLC; Rf=0.31 (C):(N,I))

($^1$H-NMR ($D_2O$); 0.80-1.90 (11H, m, —$B_{12}H_{11}$), 2.32 (4H, m, —$CH_2C\{(NH_2)(CO_2Na)\}CH_2$—), 2.64 (2H, m, $B_{12}H_{11}SCH_2$—), 2.76 (1H, m, $B_{12}H_{11}SCH_2$—))

(MS (ESI): m/z 365.2$[M+NMe_4]^{1-}$, 314.1 $[M+Na]^{1-}$, 145.6 $[M]^{2-}$, 131.2 $[B_{12}H_{11}]^{1-}$)

Example 4

Production Of ethyl 1,4-dioxaspiro[4,5]decane-8-carboxylate 8.5 g (54.4 mmol) of ethyl 4-cyclohexanocarboxylate, 3.8 ml (68.0 mmol) of ethylene glycol, and 1.1 g (5.8 mmol) of p-toluenesulfonic acid monohydrate were dissolved in 250 ml of toluene, and then the solution was refluxed for 18 hours using a Dean-Stark apparatus. After completion of the reaction, the reaction solution was concentrated under reduced pressure and 200 ml of 5% aqueous sodium hydrogen carbonate solution was added thereto. Furthermore, the reaction mixture was extracted three times with 300 ml of ether, the ether layer extracted was dried over sodium sulfate and then concentrated under reduced pressure. Then the residue was purified by silica gel column chromatography to obtain ethyl 1,4-dioxaspiro[4,5]decane-8-carboxylate (9.8 g 90%) as a pale yellow oil.

$^1$H-NMR (CDCl$_3$): 1.20 ppm (t, 3H, CH$_3$CH$_2$O—), 1.47-1.54 ppm (m, 2H, 2-CHeq, 6-CHeq), 1.71-1.80 ppm (m, 4H, 3-CH$_2$, 5-CH$_2$), 1.87-1.91 ppm (m, 2H, 2-CHax, 6-CHax), 2.23-2.31 ppm (m, 1H, 4-CH), 3.90 ppm (s, 4H, —OCH$_2$CH$_2$O—), 4.08 ppm (q, 2H, CH$_3$CH$_2$O—).

Production of 1,4-dioxaspiro[4,5]decan-8-ylmethanol

LiAlH$_4$ 2.4 g (63.2 mmol) was suspended in 100 ml of anhydrous THF, and ethyl 1,4-dioxaspiro[4,5]decane-8-carboxylate 6.7 g (31.6 mmol) obtained above was added dropwise thereto. After further refluxing for 6 hours, 100 ml of a saturated aqueous sodium hydrogen carbonate solution was gradually added dropwise at room temperature. After the mixture was filtered through Celite, the obtained filtrate was concentrated under reduced pressure. The residue was dissolved in 200 ml of ethyl acetate, and then the ethyl acetate layer was washed twice with 100 ml of a saturated aqueous sodium hydrogen carbonate solution and further with 100 ml of brine, dried over sodium sulfate, and concentrated under reduced pressure to obtain 1,4-dioxaspiro[4,5]decan-8-ylmethanol (3.8 g, 70%) as a colorless clear oil.

$^1$H-NMR (CDCl$_3$): 1.18-1.22 ppm (m, 2H, 3-CHax, 5-CHax), 1.44-1.52 (m, 3H, 3-CHeq, 4-CH, 5-CHeq), 1.70-1.72 (m, 4H, 2-CH$_2$, 6-CH$_2$), 23.40-3.44 ppm (m, 2H, HOCH$_2$—), 3.88 ppm (s, 4H, —OCH$_2$CH$_2$O—).

Production of 8-(benzyloxymethyl)-1,4-dioxaspiro[4,5]decane

At 0° C., 1.32 g (33 mmol) of 60% NaH was added to a solution containing 5.2 g (30 mmol) of 1,4-dioxaspiro[4,5]decan-8-ylmethanol dissolved in 75 ml of THF. After stirring for 10 minutes, benzyl bromide (50 mmol) was added and the mixture was stirred for 18 hours at room temperature. Then, the reaction solution was neutralized with 1N aqueous hydrochloric acid solution, and concentrated under reduced pressure. The residue was dissolved in ether, washed twice with water and once with brine, and the solvent was evaporated under reduced pressure. Then, the residue was purified by silica gel column chromatography to obtain 8-(benzyloxymethyl)-1,4-dioxaspiro[4,5]decane (6.0 g, 77%) as a colorless clear oil.

$^1$H-NMR (CDCl$_3$): 1.22-1.30 ppm (m, 2H, 3-CHax, 5-CHax), 1.48-1.56 (m, 2H, 3-CHeq, 5-CHeq), 1.61-1.82 (m, 5H, 2-CH$_2$, 4-CH, 6-CH$_2$), 3.29 ppm (d, 2H, -4CHCH$_2$—) 3.92 ppm (s, 4H, —OCH$_2$CH$_2$O—), 4.48 ppm (s, 2H, PhCH$_2$—), 7.24-7.34 ppm (m, 5H, Ar)

Production of 4-(benzyloxymethyl)cyclohexanone 5.0 g (19.1 mmol) of 8-(benzyloxymethyl)-1,4-dioxaspiro[4,5]decane was dissolved in 150 ml of 1N aqueous hydrochloric acid solution, and the solution was stirred at room temperature for one hour. The reaction solution was washed twice with 100 ml of chloroform and neutralized with sodium carbonate. The neutralized solution was extracted twice with 100 ml of ethyl acetate and the organic layer was dried over sodium sulfate and concentrated under reduced pressure to obtain 4-(benzyloxymethyl)cyclohexanone (3.7 g, 89%) as a pale yellow oil.

$^1$H-NMR (CDCl$_3$): 1.42-1.46 ppm (m, 2H, 3-CHax, 5-CHax), 2.07-2.14 (m, 3H, 3-CHeq, 4-CH, 5-CHeq), 2.31-

2.34 (m, 4H, 2-CH$_2$, 6-CH$_2$), 3.37 ppm (d, 2H, -4CHCH$_2$—), 4.51 ppm (s, 2H, PhCH$_2$—), 7.27-7.34 ppm (m, 5H, Ar).

Production of 8-benzyloxymethyl-1,3-diaza-spiro[4,5]decane-2,4-dinone 1.90 g (8.70 mmol) of 4-benzyloxymethylcyclohexanone, 853 mg (17.4 mmol) of sodium cyanide, and 4.18 g (43.5 mmol) of ammonium carbonate were dissolved in 20 ml of 50% ethanol, and after closing the reaction vessel, the reaction solution was stirred at 60° C. for 12 hours. After returning the reaction solution to room temperature, the airtight stopper of the reaction vessel was opened with sufficient caution in a draft chamber and 100 ml of water was added. The resulting precipitate was collected by filtration, washed with 100 ml of water, and recrystallized from ethyl acetate, thereby to obtain 8-benzyloxymethyl-1,3-diaza-spiro[4,5]decane-2,4-dinone (2.26 g, 90%) as a colorless crystal.

$^1$H-NMR (DMSO-d6); 1.15-1.79 (9H, m, 2-CH$_2$, 3-CH$_2$, 4-CH, 5-CH$_2$, 6-CH$_2$), 3.22 (2H, d, J=6.4 Hz, -4CHCH$_2$—), 4.44 (2H, s, PhCH$_2$—), 7.25-7.36 (5H, m, Ar), 8.41 (1H, s, NH), 10.55 (1H, s, NH)

Production of 8-hydroxymethyl-1,3-diaza-spiro[4,5]decane-2,4-dinone 1.50 g (5.20 mmol) of 8-benzyloxymethyl-1,3-diaza-spiro[4,5]decane-2,4-dinone was dissolved in 50 ml of methanol, and to this solution was added 150 mg of 10% Pd—C. The reaction solution was stirred for 24 hours at room temperature under a hydrogen atmosphere of 5.5 atm. After completion of the reaction, the palladium was removed by filtration, and the filtrate was concentrated to obtain a colorless solid, which was recrystallized from methanol, thereby to yield 8-hydroxymethyl-1,3-diaza-spiro[4,5]decane-2,4-dinone (906 mg, 88%).

$^1$H-NMR (DMSO-d6); 1.07-1.68 (9H, m, 2-CH$_2$, 3-CH$_2$, 4-CH, 5-CH$_2$, 6-CH$_2$), 3.19 (2H, dd, J=5.2 Hz, HOCH$_2$—), 4.42 (1H, t, J=5.2 Hz, OH), 8.40 (1H, s, NH), 10.55 (1H, s, NH)

Production of 8-(p-toluenesulfonyloxymethyl)-1,3-diaza-spiro[4,5]decane-2,4-dinone 500 mg (2.52 mmol) of 8-hydroxymethyl-1,3-diaza-spiro[4,5]decane-2,4-dinone and 720 mg (3.79 mmol) of tosyl chloride were dissolved in 10 ml of pyridine under nitrogen atmosphere, and the mixture was stirred at room temperature for 24 hours. After addition of 100 ml of water to the reaction solution, the resulting white precipitate was collected by filtration, and washed with 50 ml of water and 50 ml of diethyl ether, to obtain the desired 8-(p-toluenesulfonyloxymethyl)-1,3-diaza-spiro[4,5]decane-2,4-dinone (780 mg, 88%) as a colorless solid.

$^1$H NMR (DMSO-d6); 1.07-1.18 (2H, m, 3-CHax, 5-CHax), 1.47-1.58 (7H, m, 2-CH$_2$, 3-CHeq, 4-CH, 5-CHeq, 6-CH$_2$), 2.42 (3H, s, CH$_3$), 3.77 (2H, d, J=6.4 Hz, -4CHCH$_2$—), 7.48 (2H, d, J=8.0 Hz, m-Ar), 7.78 (2H, d, J=8.0 Hz, o-Ar), 8.36 (1H, s, NH), 10.58 (1H, s, NH)

Production of 8-iodomethyl-1,3-diaza-spiro[4,5]decane-2,4-dinone 500 mg (1.42 mmol) of 8-(p-toluenesulfonyloxymethyl)-1,3-diaza-spiro[4,5]decane-2,4-dinone was dissolved in acetone, to which 1.06 g (7.09 mmol) of NaI was added, followed by heating under reflux for 12 hours. The reaction solution was filtered and the obtained white precipitate was washed with 50 ml of water and 50 ml of acetone to obtain the desired 8-iodomethyl-1,3-diaza-spiro[4,5]decane-2,4-dinone (362 mg, 83%) as a colorless solid.

¹H-NMR (DMSO-d6); 1.15-1.24 (2H, m, 3-CHax, 5-CHax), 1.51-1.83 (7H, m, 2-CH₂, 3-CHeq, 4-CH, 5-CHeq, 6-CH₂), 3.10 (2H, d, J=6.4 Hz, -4CHCH₂—), 8.41 (1H, s, NH), 10.60 (1H, s, NH)

Production of 8-undecahydrododecaboranethiomethyl-1,3-diaza-spiro[4,5]decane-2,4-dinone bistetramethylammonium salt 250 mg (0.811 mmol) of 8-iodomethyl-1,3-diaza-spiro[4,5]decane-2,4-dinone and 254 mg (0.676 mmol) of 2-dodecaboranylthiopropanenitrile tetramethylammonium salt were dissolved in 10 ml of acetonitrile, and the solution was heated under reflux for 12 hours. The reaction solution was filtered, the filtrate was concentrated, the residue was dissolved in 20 ml of acetone, and 246 mg (0.676 mmol) of 25% (by weight) tetramethylammonium hydroxide was added thereto. The resulting white precipitate was collected by filtration, washed with 10 ml of acetone, and the obtained colorless solid was recrystallized from water and acetonitrile to obtain 8-undecahydrododecaboranethiomethyl-1,3-diaza-spiro[4,5]decane-2,4-dinone bistetramethyl-ammonium salt (323 mg, 97%) as a colorless crystal.

¹H-NMR (DMSO-d6); 0.55-1.76 (20H, m, B₁₂H₁₁, 2-CH₂, 3-CH₂, 4-CH, 5-CH₂, 6-CH₂), 2.13 (2H, d, J=6.4 Hz, SCH₂—), 3.09 (24H, s, NMe₄), 8.33 (1H, s, NH), 10.52 (1H, br, NH)

Production of 1-amino-4-[(undecahydrododecaboranylthio)methyl]cyclohexanone-1-carboxylic acid disodium salt 300 mg (0.609 mmol) of 8-undecahydrododecaboranethiomethyl-1,3-diaza-spiro[4,5]decane-2,4-dinone bistetramethylammonium salt was dissolved in 36 ml of 0.5N NaOH, and the solution was heated under reflux for 5 hours. After returning the reaction solution to room temperature, it was passed through a column of Amberlite IR-124 (H⁺ form) and then a column of Amberlite IR-124 (Na⁺ form). The fractions containing the desired compound were concentrated to obtain the desired 1-amino-4-[(undecahydrododecaboranylthio)methyl]cyclohexanone-1-carboxylic acid disodium salt (220 mg, 99%) as a pale yellow crystal.

¹H-NMR (D₂O); 0.75-1.65 (15H, m, B₁₂H₁₁, 2-CHax, 3-CHax, 5-CHax, 6-CHax), 1.71-1.87 (5H, m, 2-CHeq, 3-CHeq, 4-CH, 5-CHeq, 6-CHeq), 2.32 (2H, d, J=6.4 Hz, -4CHCH₂—)

(Biological Evaluation)

Cytotoxicity, uptake into cancer cells, and cell killing effect by neutron irradiation were evaluated by performing the following biological assays on the compounds (boron agents) obtained in Examples 1 to 4.

Cytotoxicity Test (WST-8)

Using a 96-well microplate, rat glima cells (C6) were seeded at a density of $1.5 \times 10^4$ cells/ml per well and then cultured at room temperature (37° C., 5% CO₂) for 16 hours. The culture fluid was taken out by suction and the culture fluids containing boron agents at various concentrations obtained in the Examples were added to respective wells in an amount of 100 ml each. After culturing at room temperature (37° C., 5% CO₂) for 48 hours, the culture fluid was taken out by suction, 100 ml portions of WST-8 solution were added respectively, and culture was further carried out at room temperature (37° C., 5% CO₂) for 4 hours. Using a microplate reader, the absorbance at a wavelength of 450 nm (reference wavelength: 655 nm) was measured and the absorbance of wells not containing cells was employed as background control, to determine each IC₅₀ value.

The IC₅₀ values of cis-1-amino-3-(dodecaboranylthiomethyl)cyclobutanecarboxylic acid trisodium salt (cis-ACBC-BSH) obtained in Example 2, trans-1-amino-3-(dodecaboranylthiomethyl)cyclobutane-carboxylic acid trisodium salt (trans-ACBC-BSH) obtained in Example 3, and 1-amino-4-[(undecahydrododecaboranyl-thio)methyl]cyclohexanone-1-carboxylic acid disodium salt (cis-ACHC-BSH) obtained in Example 4 are shown below.

In addition, 4-borono-L-phenylalanine (L-BPA), which has been used for clinical studies of BNCT, was employed as comparative example.

TABLE 1

|  | IC₅₀ | STDEV |
|---|---|---|
| L-BPA | >2 mM | — |
| cis-ACBC-BSH | 2.5 mM | 0.71 |
| trans-ACBC-BSH | 2.1 mM | 0.44 |
| cis-ACHC-BSH | <0.3 mM | — |

As a result, it was found that the compounds obtained in the Examples exhibited cytotoxicity that was at least comparable to or more than that of 4-borono-L-phenylalanine (L-BPA).

Testing of Uptake of Boron Agent by Tumor Cells $1.5 \times 10^7$ rat glima cells (C6) were seeded and cultured at room temperature (37° C., 5% $CO_2$) for 24 hours. This culture fluid was removed therefrom by suction, culture fluids containing 2.0 mM of each boron agent were added thereto, and these was cultured at room temperature (37° C., 5% $CO_2$) for 24 hours. These culture fluids were removed by suction and the cells were washed three times with PBS and treated with trypsin to recover the cells. The number of the cells recovered was counted, and $HClO_4$ (60%, 0.3 ml) and $H_2O_2$ (31%, 0.6 ml) were heated at 75° C. for one hour to prepare an ashing solution. The ashing solution was filtered by using a membrane filter and the intracellular boron concentration was determined by measuring the boron concentration in the solution using ICP-AES.

Figure 1:
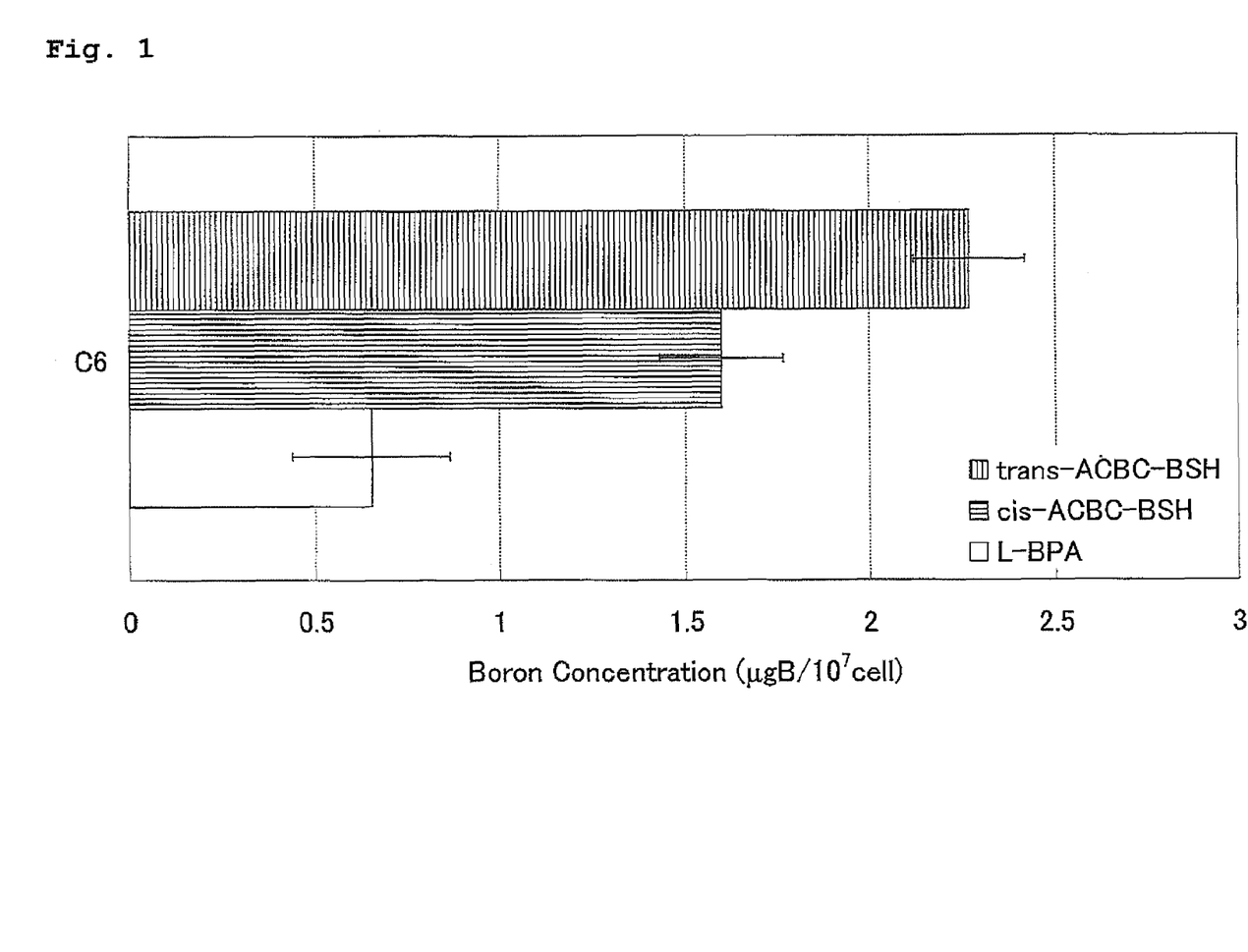
FIG. 1 shows the results of testing of uptake by tumor cells of boron compounds having amino acid skeletons containing cyclo-type rings in accordance with the present invention.

The results of testing of uptake of cis-1-amino-3-(dodecaboranylthiomethyl)cyclobutanecarboxylic acid trisodium salt (cis-ACBC-BSH) obtained in Example 2 and trans-1-amino-3-(dodecaboranylthiomethyl)cyclobutane-carboxylic acid trisodium salt (trans-ACBC-BSH) obtained in Example 3 are shown in FIG. 1. Here, 4-borono-L-phenylalanine (L-BPA), which has been used for clinical studies of BNCT, was employed as comparative example.

As a result, the fractional amount delivered to cells was found to be higher for compounds in accordance with the present invention than for 4-borono-L-phenylalanine (L-BPA).

Cell Killing Effect for Tumor Cells Subjected to Neutron Irradiation $5.0 \times 10^6$ cells were seeded and cultured at room temperature (37° C., 5% $CO_2$) for 24 hours. This culture fluid was removed therefrom by suction, culture fluids containing 2.0 mM of each boron agent were added thereto, and these were then cultured at room temperature (37° C., 5% $CO_2$) for 6 hours. These culture fluids were removed by suction and the cells were washed three times with PBS and treated with trypsin to recover the cells. The cells recovered were suspended in culture fluid, adjusted to a density of $5.0 \times 10^3$ cells/ml, and 1 ml of the suspension was transferred to a Teflon (registered trade mark) tube. The Teflon (registered trade mark) tube containing the cell solution was irradiated with thermal neutrons of 0 to $4.3 \times 10^{12}$ $cm^2$ and the cells (300 cells each) were seeded in 6 ml of culture fluid. Culture was carried out at room temperature (37° C., 5% $CO_2$) for 9 days and the colony or colonies was or were immobilized with ethanol, stained with 0.1% crystal violet, and the number of colonies was counted for comparison of cell killing effect.

Figure 2:
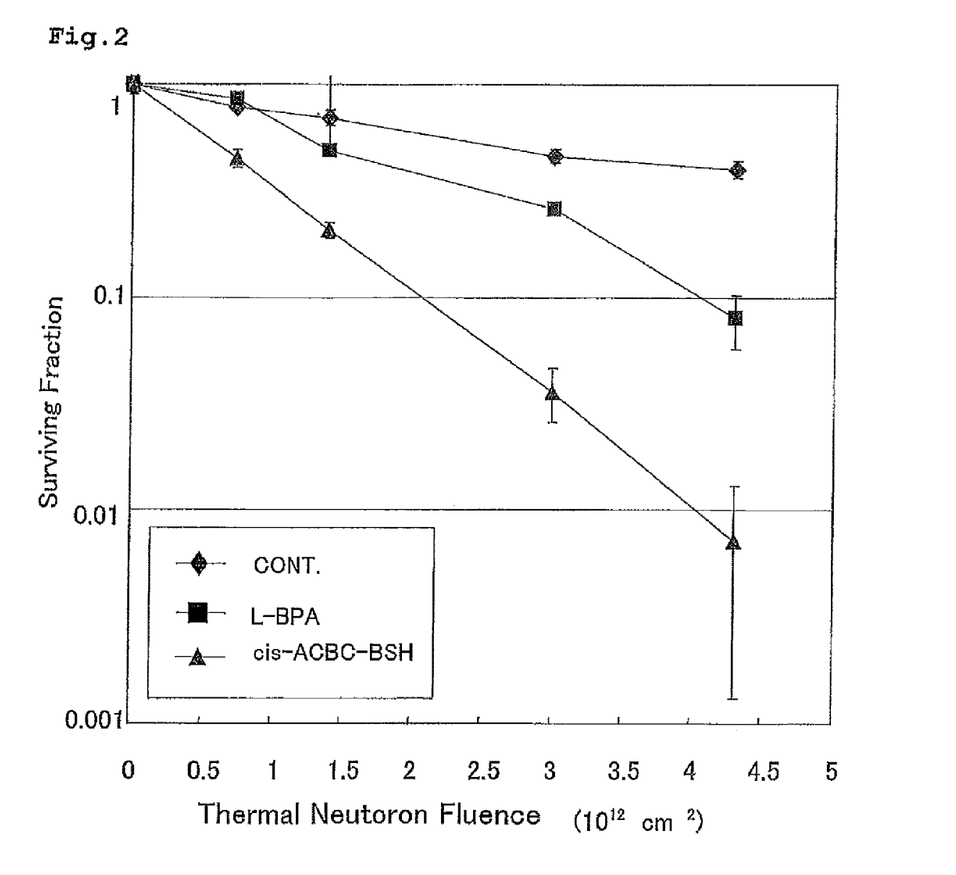
FIG. 2 shows the cell killing effect of a boron compound having an amino acid skeleton containing a cyclo-type ring in accordance with the present invention when the boron compound is used on tumor cells which are irradiated with neutrons.

The cell killing effect of cis-1-amino-3-(dodecaboranylthiomethyl)cyclobutanecarboxylic acid trisodium salt (cis-ACBC-BSH) obtained in Example 2 is shown in FIG. 2. 4-Borono-L-phenylalanine (L-BPA), which has been used for clinical studies of BNCT, was employed as comparative example.

As a result, the cell killing effect of the compound of the present invention was found to be higher than that of 4-borono-L-phenylalanine (L-BPA).

The invention claimed is:

1. A boron compound having an amino acid skeleton containing a cyclo-type ring, represented by the general formula (I):

[Formula 1]

wherein l represents an integer of 1 to 6; m is 0, 1, or 2; and n is 0, 1, or 2; or a pharmaceutically acceptable salt thereof.

2. The boron compound having an amino acid skeleton containing a cyclo-type ring or a pharmaceutically acceptable salt thereof according to claim 1, wherein l is 1, m is 0 or 1, and n is 0 or 1.

3. The boron compound having an amino acid skeleton containing a cyclo-type ring or a pharmaceutically acceptable salt thereof according to claim 1, which is represented by the general formula (II):

[Formula 2]

wherein l represents an integer of 1 to 6.

4. The boron compound having an amino acid skeleton containing a cyclo-type ring or a pharmaceutically acceptable salt thereof according to claim 1, which is represented by the general formula (III):

[Formula 3]

wherein l represents an integer of 1 to 6.

5. A method for producing a boron compound having an amino acid skeleton containing a cyclo-type ring, the method comprising the step of reacting a cyanoethyl BSH (1) represented by the general formula (1):

[Formula 4]

with a compound (2) represented by the general formula (2):

[Formula 5]

wherein X is a halogen, l represents an integer of 1 to 6, m is 0, 1, or 2, and n is 0, 1, or 2, in the presence of an alkali.

6. A method for producing a boron compound having an amino acid skeleton containing a cyclo-type ring, the method comprising the step of reacting a cyanoethyl BSH (1) represented by the general formula (1) with a compound (3) represented by the general formula (3):

[Formula 6]

(3)

wherein X is a halogen, l represents an integer of 1 to 6, m is 0, 1, or 2, and n is 0, 1, or 2, in the presence of an alkali.

7. The boron compound having an amino acid skeleton containing a cyclo-type ring or a pharmaceutically acceptable salt thereof according to claim 1, wherein l is 1, m is 0, and n is 0.

8. The boron compound having an amino acid skeleton containing a cyclo-type ring or a pharmaceutically acceptable salt thereof according to claim 1, wherein l is 1, m is 1, and n is 1.

9. A salt of boron compound having an amino acid skeleton containing a cyclo-type ring according to claim 7, wherein the salt is a sodium salt.

10. A salt of boron compound having an amino acid skeleton containing a cyclo-type ring according to claim 8, wherein the salt is a sodium salt.

* * * * *